(12) United States Patent
Hong et al.

(10) Patent No.: US 10,550,142 B2
(45) Date of Patent: Feb. 4, 2020

(54) QUERCETIN-BASED COMPOUND

(71) Applicant: AMOREPACIFIC CORPORATION, Seoul (KR)

(72) Inventors: Yong-Deog Hong, Yongin-si (KR); Minsik Choi, Yongin-si (KR); Si Young Cho, Yongin-si (KR); Jeong-Kee Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/343,307

(22) PCT Filed: Oct. 16, 2017

(86) PCT No.: PCT/KR2017/011404
§ 371 (c)(1),
(2) Date: Apr. 18, 2019

(87) PCT Pub. No.: WO2018/074794
PCT Pub. Date: Apr. 26, 2018

(65) Prior Publication Data
US 2019/0241601 A1     Aug. 8, 2019

(30) Foreign Application Priority Data

Oct. 18, 2016 (KR) ........................ 10-2016-0135299

(51) Int. Cl.
| | | |
|---|---|---|
| *C07H 17/07* | (2006.01) | |
| *C12P 19/60* | (2006.01) | |
| *A61K 31/7048* | (2006.01) | |
| *A61K 36/82* | (2006.01) | |

(52) U.S. Cl.
CPC ......... *C07H 17/07* (2013.01); *A61K 31/7048* (2013.01); *A61K 36/82* (2013.01); *C12P 19/60* (2013.01)

(58) Field of Classification Search
None
See application file for complete search history.

(56) References Cited

PUBLICATIONS

Itoh et al., Journal of Natural Products, vol. 67(3), pp. 427-431 (Year: 2004).*
International Search Report and Written Opinion from International Application No. PCT/KR2017/011404, dated Jan. 24, 2018.
Xi-Feng Teng, et al., "Five New Flavonol Glycosides from the Fresh Flowers of Camellia reticulata", Helvetica Chimica Acta, Jul. 21, 2008, vol. 91, No. 7, pp. 1305-1312.
Lu-Rong Xu, et al., "A new acylated flavonol glycoside from Derris triofoliata" Journal of Asian Natural Products Research, 2006, vol. 8, No. 1-2, pp. 9-13.
Md. Maniruzzaman Manir, et al., "Tea catechins and flavonoids from the leaves of Camellia sinensis inhibit yeast alcohol dehydrogenase", Bioorganic & Medicinal Chemistry, 2012, vol. 20, No. 7, pp. 2376-2381.
G. W. Plumb, et al., "Antioxidant properties of flavonol glycosides from tea", Redox Report, 1999, vol. 4, No. 1-2, pp. 13-16.
Keith R. Price, et al., "Flavonol Glycoside Content and Composition of Tea Infusions Made from Commercially Available Teas and Tea Products", J. Agric. Food Chem., 1998, vol. 46, No. 7, pp. 2517-2522.

* cited by examiner

*Primary Examiner* — Traviss C McIntosh, III
(74) *Attorney, Agent, or Firm* — Merchant & Gould P.C.

(57) ABSTRACT

The present specification relates to a novel quercetin-based compound separated from post fermented tea, an isomer thereof, a pharmaceutically acceptable salt thereof, a hydrate thereof or a solvate thereof, the compound being capable of being widely used in post fermented tea-related industries and various fields in which the compound may be used.

7 Claims, 11 Drawing Sheets

QUERCETIN-BASED COMPOUND

This application is a National Stage Application of International Application No. PCT/KR2017/011404, filed 16 Oct. 2017, which claims benefit of Serial No. 10-2016-0135299, filed 18 Oct. 2016 in the Republic of Korea and which applications are incorporated herein by reference. To the extent appropriate, a claim of priority is made to each of the above disclosed applications.

TECHNICAL FIELD

The present specification relates to a novel quercetin-based compound.

BACKGROUND ART

Green tea is drunk as a coarse tea, which is in the form of leaves, or drunk as a fermented tea to feel a deeper flavor. Fermented green tea means that the green tea leaves have been oxidized. It includes fermented teas oxidized by oxidases present in tea leaves and post fermented teas fermented by microorganisms other than the enzymes present in tea leaves. It can be classified into weakly fermented tea, semi-fermented tea, fully fermented tea, etc. according to the degree of fermentation. Fermented green tea is referred to as various names such as green tea, oolong tea, black tea, and pu'er tea depending on the type and degree of fermentation.

The countries with the world's leading technology for producing post fermented tea are China and Japan. The aerobically fermented Chinese teas are produced using fungi as the fermentation strains and mainly cultivated in West Xishuangbanna, Yunnan province. The aerobically fermented Japanese teas include dark tea, which is produced using fungi as the fermentation strains and mainly cultivated in Toyama. The anaerobically fermented Japanese teas include Bancha, which is produced using anaerobic *Lactobacillus* as the fermentation strain and mainly cultivated in Awa, and black tea, which is produced using anaerobic fungi as the fermentation strains and mainly cultivated in Ishizuchi. Traditional pu'er tea, which originated from the city of Pu'er in China, is produced by deliberately harming green tea leaves when harvesting them, heating and roasting them, applying an appropriate amount of water, and naturally fermenting them using microorganisms in the air. In Korea, fermented teas are produced for consumption intermittently by a cottage industry in Mt. Jiri and Boryeong.

Fermented teas are different from coarse teas in flavor. They may also show a large difference in the type and content of active ingredients depending on the specific fermentation process and the type of microorganism. As such, various compounds can be generated and separated therefrom, and thus various attempts have been made to separate and identify unknown novel compounds using green tea.

Quercetin-based compounds are a type of flavonoids, and most of them exist as glycosides in nature, which include quercitrin, isoquercitrin, quercimeritrin, avicularin, hyperin, reynoutrin, querciturone, and rutin, depending on the type of saccharides.

SUMMARY OF INVENTION

Technical Problem

In one aspect, an object of the present invention is to discover a novel quercetin-based compound from post fermented tea and utilize it industrially.

In another aspect, an object of the present invention is to provide a method for preparing the novel quercetin-based compound to enhance its industrial applicability.

Solution to Problem

In order to achieve the above objects, the present invention according to one aspect provides a compound represented by the following formula 1, an isomer thereof, a pharmaceutically acceptable salt thereof, a hydrate thereof, or a solvate thereof:

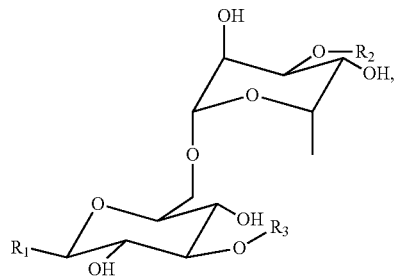

Formula 1 wherein $R_1$ may be $C_{15}H_9O_7$, $R_2$ may be H or $C_6H_{11}O_5$, and $R_3$ may be $C_9H_7O_2$.

In another aspect, the present invention provides a method for preparing the compound, an isomer thereof, a pharmaceutically acceptable salt thereof, a hydrate thereof or a solvate thereof.

Advantageous Effects of Invention

In one aspect, the present invention allows to separate a specific novel compound from post fermented tea and utilize it industrially so that it can be widely used in post fermented tea-related industries and various fields in which the compound may be used, thereby meeting the demand of related consumers.

DESCRIPTION OF EMBODIMENTS

Embodiments

Figure 1:
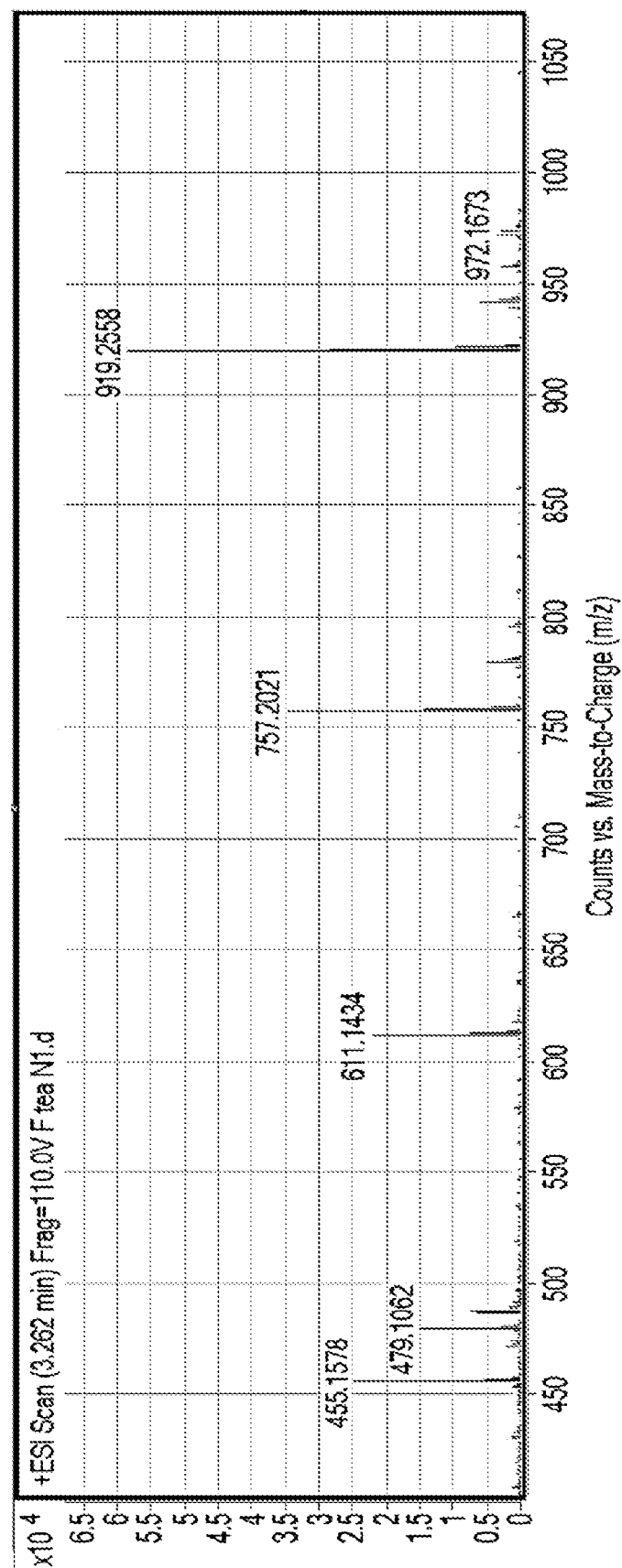
FIG. 1 shows the MS spectrum of quercetin 3-O-[3-O"-(E)-p-coumaroyl][β-D-glucopyranosyl-(1→3)-O-α-L-rhamnopyranosyl-(1→6)-O-β-D-glucopyranoside].

As used herein, the term "post fermented" encompasses fermentation using a microorganism or substance other than the enzymes present in tea leaves. The post fermented tea encompasses green teas fermented by the above method.

As used herein, the term "fraction" covers those obtained by fractionating a specific substance or extract using a certain solvent or those left after fractionation and those obtained by extracting them with a specific solvent again. The fractionation method and the extraction method may be any method known to those skilled in the art.

As used herein, the "isomer" includes not only optical isomers (e.g., essentially pure enantiomers, essentially pure diastereomers or a mixture thereof) but also conformational isomers (i.e., isomers in which only the angle of one or more chemical bonds is different between each other), positional isomers (particularly, tautomers), or geometric isomers (e.g., cis-trans somers).

As used herein, "essentially pure" means, when used, for example, with regard to enantiomers or diastereomers, that specific compounds, e.g., enantiomers or diastereomers, are present in an amount of about 90% (w/w) or more, preferably about 95% or more, more preferably about 97% or more or about 98% or more, more preferably about 99% or more, even more preferably about 99.5% or more.

As used herein, "pharmaceutically acceptable" means being devoid of substantial toxic effects when used in a usually employed medicinal dosage and thereby being approvable or approved by the government or a regulatory organization comparable thereto or being listed in the Pharmacopeia or recognized by other general pharmacopoeias for use in animals, and more particularly in humans.

As used herein, the "pharmaceutically acceptable salt" refers to a salt according to one aspect of the present invention that is pharmaceutically acceptable and possesses the desired pharmacological activity of the parent compound. Such salts include: (1) acid addition salts formed from an inorganic acid such as hydrochloric acid, hydrobromic acid, sulfuric acid, nitric acid, phosphoric acid, etc., or formed from an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid and muconic acid; or (2) salts formed when an acidic proton present in the parent compound is substituted.

As used herein, the "hydrate" refers to a compound to which water is bonded. The term is used in a broad sense, including an inclusion compound which lacks chemical bonding with water.

As used herein, the "solvate" refers to a high order compound formed between a molecule or ion of solute, and a molecule or ion of solvent.

In one aspect, the present invention provides a compound represented by the following formula 1, an isomer thereof, a pharmaceutically acceptable salt thereof, a hydrate thereof or a solvate thereof:

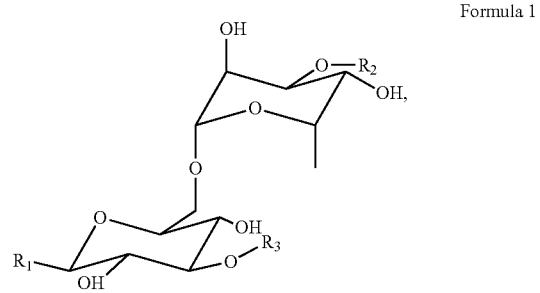

Formula 1 wherein $R_1$ may be $C_{15}H_9O_7$, $R_2$ may be H or $C_6H_{11}O_5$, and $R_3$ may be $C_9H_7O_2$.

In one embodiment, $R_1$ may be a compound represented by the following formula 2:

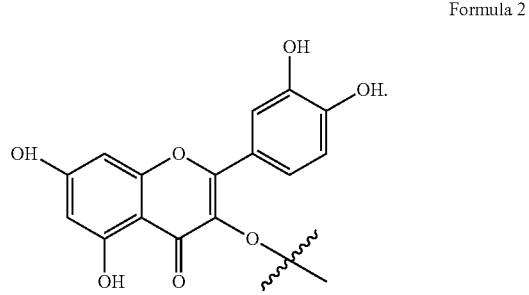 [SMILES: *Oc1c(-c2ccc(O)c(O)c2)oc2cc(O)cc(O)c2c1=O]

Formula 2

In another embodiment, $R_2$ may be a compound represented by the following formula 3:

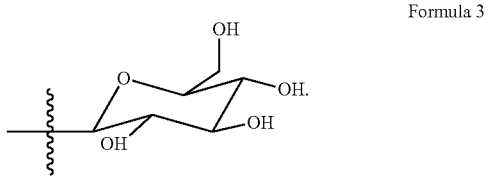 [SMILES: *C1OC(CO)C(O)C(O)C1O]

Formula 3

$R_3$ may be a compound represented by the following formula 4:

Formula 4

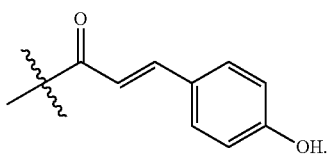

In another embodiment, the compound may be quercetin 3-O-[3-O"-(E)-p-coumaroyl][β-D-glucopyranosyl-(1→3)-O-α-L-rhamnopyranosyl-(1→6)-O-β-D-glucopyranoside]. Quercetin 3-O-[3-O"-(E)-p-coumaroyl][β-D-glucopyranosyl-(1→3)-O-α-L-rhamnopyranosyl-(1→6)-O-β-D-glucopyranoside] can be represented by the following formula:

Formula 5

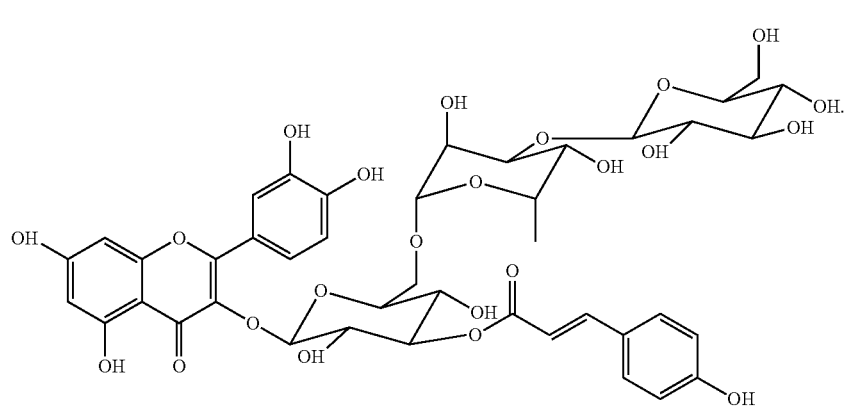

In another embodiment, the compound may be quercetin 3-O-[3-O"-(E)-p-coumaroyl][α-L-rhamnopyranosyl-(1→6)-O-β-D-glucopyranoside]. Quercetin 3-O-[3-O"-(E)-p-coumaroyl][α-L-rhamnopyranosyl-(1→6)-O-β-D-glucopyranoside] can be represented by the following formula:

Formula 6

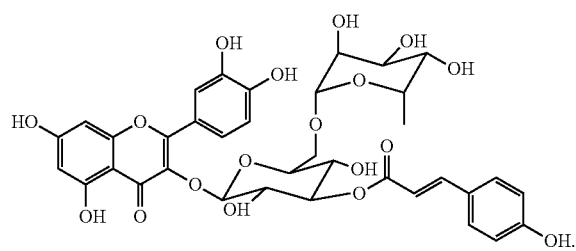

In one aspect, the present invention relates to a novel substance which is not known in the prior art. The present inventors have discovered and separated the novel substance after continuous research on post fermented tea. The compound according to one aspect of the present invention has usefulness such as inhibition of beta amyloid aggregation (see FIG. 11).

Beta amyloid aggregation is a clinically applicable property in medicines and related fields, and thus it can be clearly understood that the present invention is industrially applicable.

Further studies on the usefulness of the compound could allow the compound to be used in a variety of industrial applications.

In one embodiment, the content of the compound may be 0.01% by weight or more, 0.05% by weight or more, 0.1% by weight or more, 0.2% by weight or more, 0.3% by weight or more, 0.4% by weight or more, 0.5% by weight or more, 0.7% by weight or more, 0.9% by weight or more, 1.0% by weight or more, 1.3% by weight or more, 1.5% by weight or more, 1.7% by weight or more, 2.0% by weight or more, 2.2% by weight or more, 2.5% by weight or more, 2.8% by weight or more, 3.0% by weight or more, 3.3% by weight or more, 3.5% by weight or more, 3.8% by weight or more, 4.0% by weight or more, 4.5% by weight or more, 5.0% by weight or more, 5.5% by weight or more, 6.0% by weight or more, 8.0% by weight or more, 10% by weight or more, 12% by weight or more, 15% by weight or more, or 20% by weight or more. Also, it may be 18% by weight or less, 15% by weight or less, 12% by weight or less, 10% by weight or less, 8.0% by weight or less, 6.0% by weight or less, 5.5% by weight or less, 5.0% by weight or less, 4.5% by weight or less, 4.0% by weight or less, 3.8% by weight or less, 3.5% by weight or less, 3.3% by weight or less, 3.0% by weight or less, 2.8% by weight or less, 2.5% by weight or less, 2.2% by weight or less, 2.0% by weight or less, 1.7% by weight or less, 1.5% by weight or less, 1.3% by weight or less, 1.0% by weight or less, 0.9% by weight or less, 0.8% by weight or less, 0.7% by weight or less, 0.5% by weight or less, 0.4% by weight or less, 0.3% by weight or less, 0.2% by weight or less, 0.1% by weight or less, 0.05% by weight or less, or 0.03% by weight or less.

In another aspect, the present invention provides a method for preparing the compound, an isomer thereof, a pharmaceutically acceptable salt thereof, a hydrate thereof or a solvate thereof. The preparation method may include synthesis, separation from natural products, etc.

In one embodiment, the preparation method may be fermenting green tea and then separating it. The preparation method may include the step of inoculating a fermentation organism into green tea leaves, fermenting them, drying them with hot air and allowing them to age. It may also include the step of, after aging, performing extraction and fractionation to separate the compound.

The extraction and fractionation may be performed using water, an organic solvent or the like, and employ any method known to those skilled in the art.

In another aspect, the fractionation may be performed after the extraction. It may be performed using ketone, or may be performed by extracting those fractionated with ketone using an alcohol (for example, ethanol). Examples of the ketone include acetone, carvone, pulegone, isolongifolanone, 2-heptanone, 2-pentanone, 3-hexanone, 3-heptanone, 4-heptanone, 2-octanone, 3-octanone, 2-nonanone, 3-nonanone, 2-undecanone, 2-tridecanone, methyl isopropyl ketone, ethyl isoamyl ketone, butylidene acetone, methyl heptenone, dimethyl octenone, geranyl acetone, farnesyl acetone, 2,3-pentadione, 2,3-hexadione, 3,4-hexanedione, 2,3-heptadione, amyl cyclopentanone, amyl cyclopentenone, 2-cyclopentyl cyclopentanone, hexyl cyclopentanone, 2-n-heptyl cyclopentanone, cis-jasmone, dihydrojasmone, methyl corylone, 2-tert-butyl cyclohexanone, p-tert-butylcyclohexanone, 2-sec-butylcyclohexanone, celery ketone, cryptone, p-tert-pentyl cyclohexanone, methyl cyclocitrone, nerone, 4-cyclohexyl-4-methyl-2-pentanone, oxide ketone, emoxyfurone, methyl naphthyl ketone, α-methylanisalacetone, anisyl acetone, p-methoxyphenyl acetone, benzylidene acetone, p-methoxyacetophenone, p-methylacetophenone, propiophenone, acetophenone, α-dynascone, iritone, ionone, pseudoionone, methyl ionone, methyl iritone, 2,4-di-tert-butylcyclohexanone, allyl ionone, 2-acetyl-3,3-dimethylnorbornane, verbenone, fenchone, cyclopentadecanone, and cyclohexadecenone. Examples of the ketone also include ketones as solvents which can be generally used in the art and mixtures thereof, and preferably may be acetone.

In another embodiment, the fermentation may be performed by a post-fermentation method. The post-fermentation may be performed by strain inoculation, and the strain may be a strain selected from the group consisting of *Saccharomyces* sp., *Bacillus* sp., *Lactobacillus* sp., and *Leuconostoc mesenteroides* sp. Preferably, it may be selected from *Saccharomyces cerevisiae, Lactobacillus casei, Bacillus subtlis, Lactobacillus bulgarius*, and *Leuconostoc mesenteroides*.

Hereinafter, the constitution and effects of the present invention will be described in more detail through examples and test examples. However, the following examples are provided for illustrative purposes only to facilitate understanding of the present invention, and the scope of the present invention is not limited thereto.

Example 1: Preparation of a Post Fermented Tea Sample

Water was added to a green tea made of *Camellia sinensis* var. *Yabukita* leaves to adjust the water content to 40% by weight. The resultant was inoculated with $5\times10^6$ cfu/g of *Bacillus subtillis*, followed by fermentation at 50° C. for 3 days and further fermentation at 80° C. for 4 days.

The aged tea sample was pulverized for 15 seconds, and then sieved with a stainless steel sieve having a mesh size of 1 mm. Then, 50 mg of the pulverized product was added to a 1.5 ml Eppendorf tube, and 1 ml of deionized water was added thereto. The mixture was stirred at a constant rate for 30 minutes in a constant-temperature water bath at 60° C., and then centrifuged at 25° C. and 13,000 rpm for 15 minutes. The water-insoluble part of the dried fermented green tea extract was separated.

Example 2: Acquisition of Fractions and Separation of Compounds 150 g of the post fermented tea sample was fractionated with acetone to remove catechin derivatives and caffeine and obtain solubles rich in the other compounds. 40 g of the acetone solubles were first fractionated by silica gel column chromatography using a 5:1 (v/v) mixture of chloroform and methanol as the solvent.

8.9 g of the caffeine-free fraction obtained with chloroform and methanol at 5:1 (v/v) was fractionated using high-performance countercurrent chromatography (HP-CCC, Dynamic Extractions Ltd, UK). The solvent used was n-hexane-TBME (methyl tert-butyl ether)-BuOH-MeCN-Water (0.25:3:1:1:5, v/v) and the flow rate was 25 ml/min. The fraction was divided into 10 subfractions under the above conditions, and the ingredients contained in each fraction were separated using small volume HPCCC (Dynamic Extractions Ltd, UK), HPLC (high-performance liquid chromatography), Sephadex LH-20 column (GE Healthcare Bio-Sciences, Sweden), etc.

As a result, quercetin 3-O-[3-O"-(E)-p-coumaroyl][β-D-glucopyranosyl-(1→3)-O-α-L-rhamnopyranosyl-(1→6)-O-β-D-glucopyranoside] and quercetin 3-O-[3-O"-(E)-p-coumaroyl][α-L-rhamnopyranosyl-(1→6)-O-β-D-glucopyranoside], which are compounds not known in the prior art, were separated from the fraction. Also, the structure of each compound was identified using $^1H$, $^{13}C$-NMR (nuclear magnetic resonance spectroscopy), UV (ultraviolet spectroscopy), and ESI-MS (electrospray ionization mass spectroscopy). For $^1H$ and $^{13}C$ nuclear magnetic resonance (NMR), methanol-d3 was used as the solvent and Bruker Advance DPX-500 (BRUKER, USA) was used as the instrument. The MS spectrum of each compound was analyzed using 6200 Series Accurate-Mass Time-of-Flight (TOF) LC/MS (Agilent, US).

As a result of the analysis, it was found that the compounds, which are novel compounds not known in the prior art, are quercetin 3-O-[3-O"-(E)-p-coumaroyl][β-D-glucopyranosyl-(1→3)-O-α-L-rhamnopyranosyl-(1→6)-O-β-D-glucopyranoside], represented by $C_{42}H_{46}O_{23}$ and having the molecular weight of 918.2430, and quercetin 3-O-[3-O"-(E)-p-coumaroyl][α-L-rhamnopyranosyl-(1→6)-O-β-D-glucopyranoside], represented by $C_{36}H_{36}O_{18}$ and having the molecular weight of 756.1902.

The formula and NMR data of quercetin 3-O-[3-O"-(E)-p-coumaroyl][β-D-glucopyranosyl-(1→3)-O-α-L-rhamnopyranosyl-(1→6)-O-β-D-glucopyranoside] are as follows:

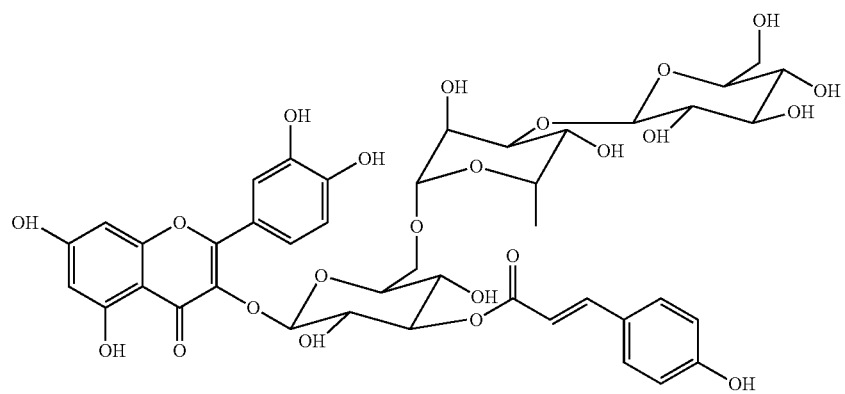 [SMILES: CC1OC(OCC2OC(Oc3c(-c4ccc(O)c(O)c4)oc4cc(O)cc(O)c4c3=O)C(O)C(OC(=O)/C=C/c3ccc(O)cc3)C2O)C(O)C(OC2OC(CO)C(O)C(O)C2O)C1O]

TABLE 1

| Position | $^{13}$C-NMR | $^{1}$H-NMR |
|---|---|---|
| 2 | 159.29 | |
| 3 | 135.58 | |
| 4 | 179.33 | |
| 5 | 163.02 | |
| 6 | 99.98 | 6.21 (H6, brs) |
| 7 | 166.03 | |
| 8 | 94.95 | 6.41 (H8, brs) |
| 9 | 158.58 | |
| 10 | 105.6 | |
| 1' | 123.06 | |
| 2' | 117.79 | 7.68 (H2', m) |
| 3' | 145.86 | |
| 4' | 149.82 | |
| 5' | 116.13 | 6.86 (H5', d, J = 8.3 Hz) |
| 6' | 123.48 | 7.62 (H6', dd, J = 8.3, 1.3 Hz) |
| p-coumaric acid | | |
| 1''' | 127.3 | |
| 2''', 6''' | 131.18 | 7.48 (H2'''/H6''', d, J = 7.8 Hz) |
| 3''', 5''' | 116.83 | 6.81 (H3'''/H5''', d, J = 7.8 Hz) |
| 4''' | 161.27 | |
| 7''' | 115.45 | 6.42 (H7''', d, J = 15.4 Hz) |
| 8''' | 146.71 | 7.68 (H8''', m) |
| C=O | 168.95 | |
| Glc1 | | |
| 1'' | 104.5 | 5.26 (H1'', d, J = 7.7 Hz) |
| 2'' | 74.11 | 3.71 (H2'', d, J = 9 Hz) |
| 3'' | 78.93 | 5.11(H3'', t, J = 9 Hz) |
| 4'' | 69.43 | 3.54 (H4'', dd, J = 9.8, 9.3 Hz) |
| 5'' | 77.54 | 3.40 (H5'', m) |
| 6'' | 68.43 | 3.80 (H6'', brd, J = 10.4 Hz) 3.49 |
| Rha | | |
| 1'''' | 102.33 | 4.57 (H1'''', brs) |
| 2'''' | 70.89 | 3.38 (H2'''', m) |
| 3'''' | 83.06 | 3.63 (H3'''', dd, J = 8.9, 2.2 Hz) |
| 4'''' | 72.6 | 3.46 (H4'''', m) |
| 5'''' | 69.76 | 3.54 (H5'''', m) |
| 6'''' | 17.96 | 1.10 (H6'''', d, J = 5.7 Hz) |
| Glc2 | | |
| 1''''' | 105.67 | 4.44 (H1''''', d, J = 7.5 Hz) |
| 2''''' | 75.48 | 3.25 (H2''''', m) |
| 3''''' | 76.97 | 3.50 (H3''''', m) |
| 4''''' | 71.28 | 3.96 (H4''''', brs) |
| 5''''' | 77.54 | 3.26 (H5''''', m) |
| 6''''' | 62.1 | 3.78-3.72 (H6''''', m) |

Figure 2:
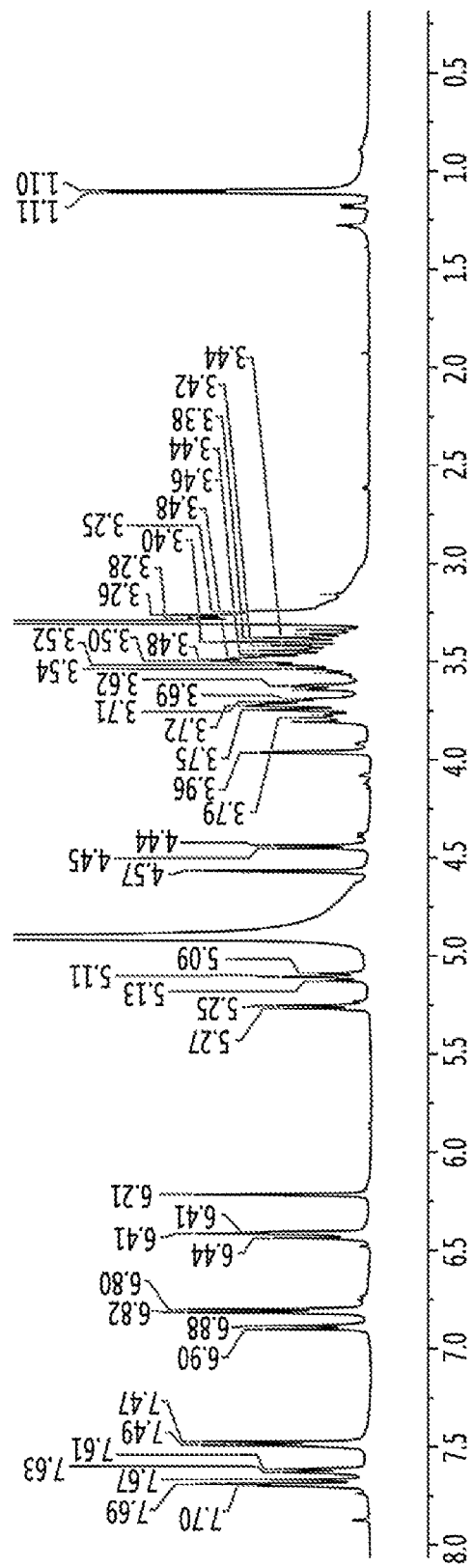
FIG. 2 shows the 1H-NMR (nuclear magnetic resonance) spectrum of quercetin 3-O-[3-O"-(E)-p-coumaroyl][β-D-glucopyranosyl-(1→3)-O-α-L-rhamnopyranosyl-(1→6)-O-β-D-glucopyranoside].
Figure 3:
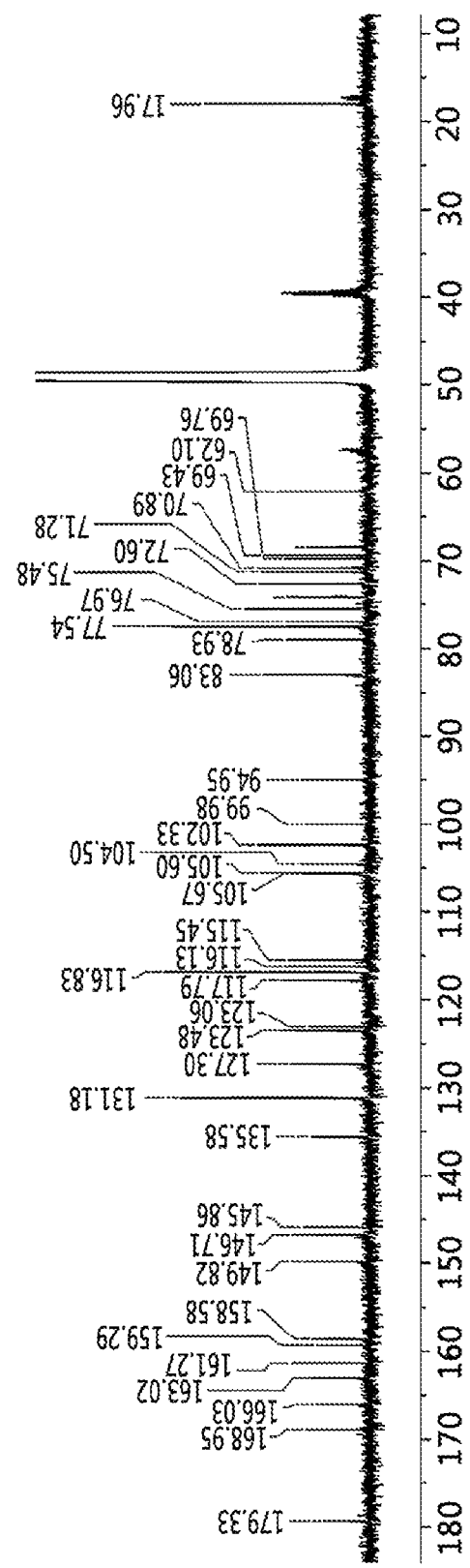
FIG. 3 shows the $^{13}$C-NMR spectrum of quercetin 3-O-[3-O"-(E)-p-coumaroyl][β-D-glucopyranosyl-(1→3)-O-α-L-rhamnopyranosyl-(1→6)-O-β-D-glucopyranoside].
Figure 4:
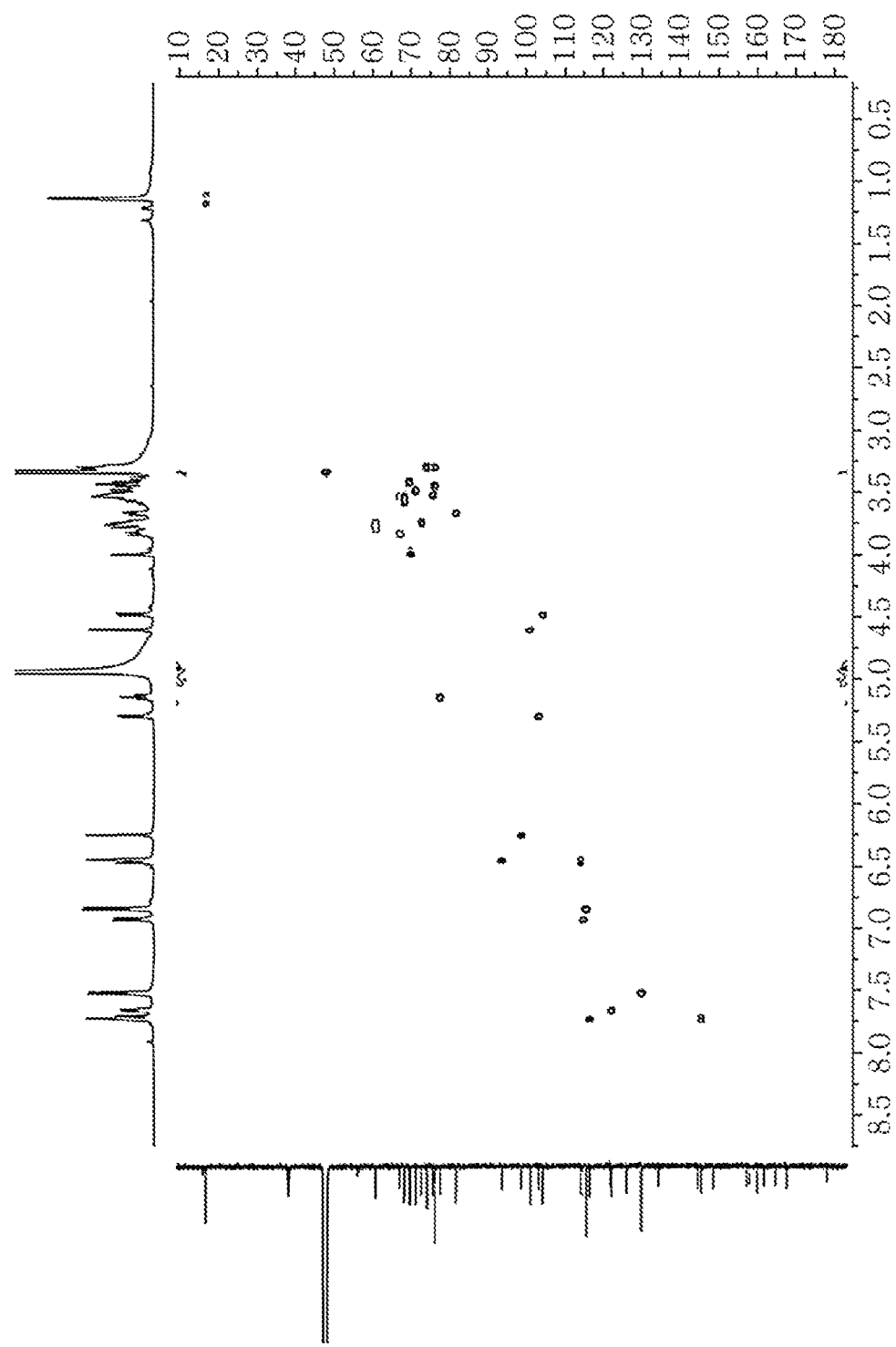
FIG. 4 shows the $^1$H-$^{13}$C HSQC (heteronuclear single quantum coherence) spectrum of quercetin 3-O-[3-O"-(E)-p-coumaroyl][β-D-glucopyranosyl-(1→3)-O-α-L-rhamnopyranosyl-(1→6)-O-β-D-glucopyranoside].
Figure 5:
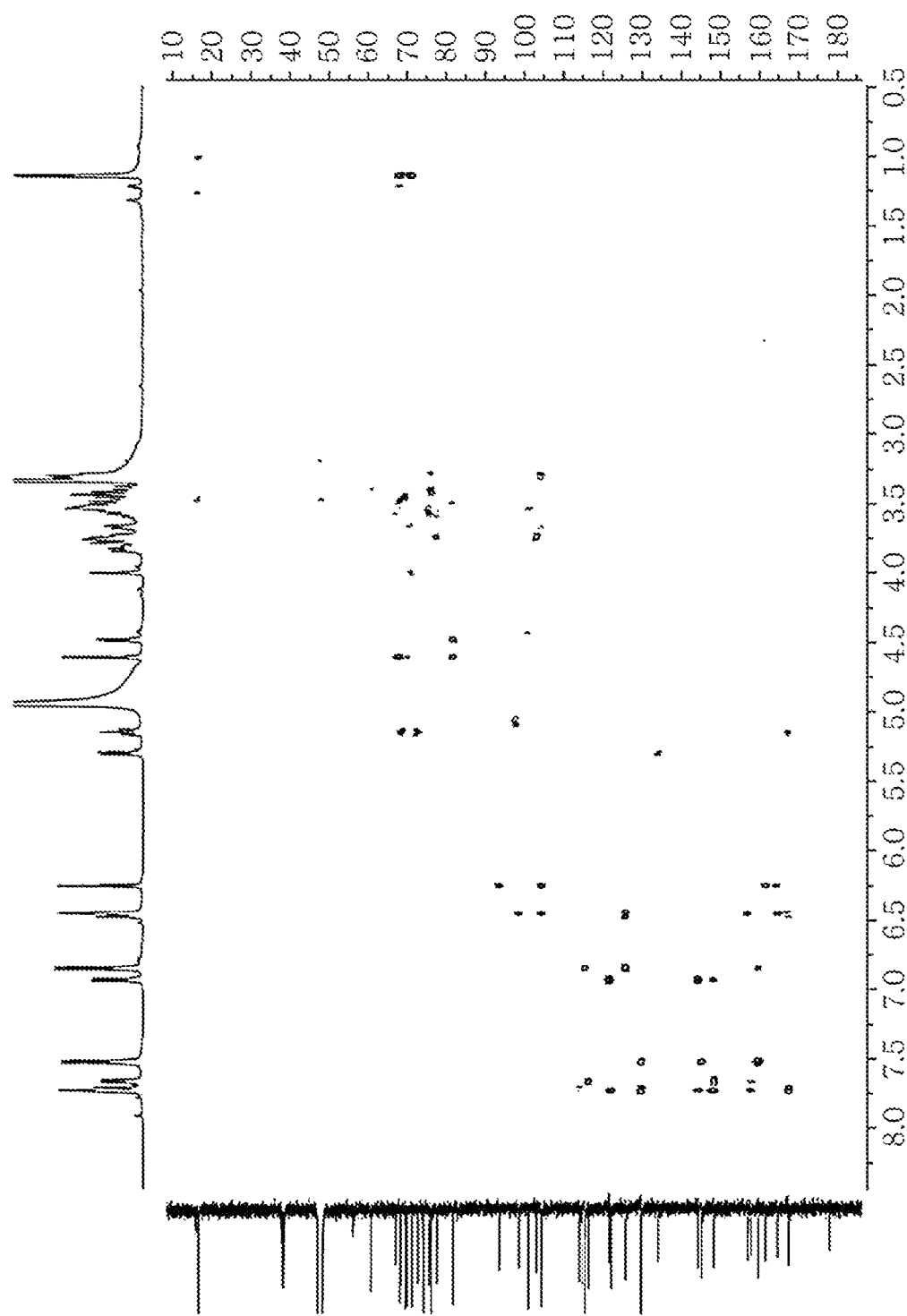
FIG. 5 shows the $^1$H-$^{13}$C HMBC (heteronuclear multiple-bond coherence) spectrum of quercetin 3-O-[3-O"-(E)-p-coumaroyl][β-D-glucopyranosyl-(1→3)-O-α-L-rhamnopyranosyl-(1→6)-O-β-D-glucopyranoside].

The MS spectrum of quercetin 3-O-[3-O''-(E)-p-coumaroyl][3-D-glucopyranosyl-(1→3)-O-α-L-rhamnopyranosyl-(1→6)-O-β-D-glucopyranoside] is as shown in FIG. 1, and the $^{1}$H-NMR spectrum and the $^{13}$C-NMR spectrum thereof are as shown in FIG. 2 and FIG. 3, respectively. The HSQC (heteronuclear single quantum coherence) spectrum thereof is as shown in FIG. 4, and the HMBC (heteronuclear multiple-bond coherence) spectrum thereof is as shown in FIG. 5.

The formula and NMR data of quercetin 3-O-[3-O''-(E)-p-coumaroyl][α-L-rhamnopyranosyl-(1→6)-O-β-D-glucopyranoside] are as follows:

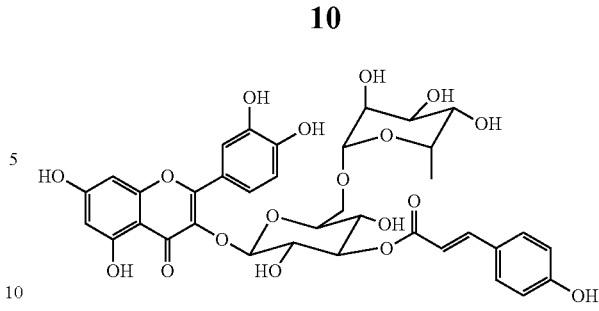

TABLE 2

| Position | $^{13}$C-NMR | $^{1}$H-NMR |
|---|---|---|
| 2 | 159.23 | |
| 3 | 135.52 | |
| 4 | 179.33 | |
| 5 | 163.02 | |
| 6 | 99.96 | 6.21 (H6, brs) |
| 7 | 166.04 | |
| 8 | 94.85 | 6.40 (H8, brs) |
| 9 | 158.52 | |
| 10 | 105.64 | |
| 1' | 123.06 | |
| 2' | 117.68 | 7.67 (H2', d, J = 8.7 Hz) |
| 3' | 145.88 | |
| 4' | 149.86 | |
| 5' | 116.11 | 6.89 (H5', d, J = 8.4 Hz) |
| 6' | 123.52 | 7.63 (H6', dd, J = 8.4, 1.7 Hz) |
| p-coumaric acid | | |
| 1''' | 127.29 | |
| 2''', 6''' | 131.17 | 7.48 (H2'''/H6''', d, J = 8.4 Hz) |
| 3''', 5''' | 116.82 | 6.81 (H3'''/H5''', d, J = 8.4 Hz) |
| 4''' | 161.26 | |
| 7''' | 115.44 | 6.42 (H7''', d, J = 15.7 Hz) |
| 8''' | 146.7 | 7.68 (H8''', d, J = 15.7 Hz) |
| C=O | 168.97 | |
| Glc1 | | |
| 1'' | 101.55 | 5.28 (H1'', d, J = 7.8 Hz) |
| 2'' | 74.14 | 3.71 (2'', d, J = 9 Hz) |
| 3'' | 73.25 | 5.11 (H3'', t, J = 9.2 Hz) |
| 4'' | 70.47 | 3.54 (H4'', dd, J = 9.8, 9.3 Hz) |
| 5'' | 75.51 | 3.40 (H5'', m) |
| 6'' | 67.54 | 3.80 (H6'', brd, J = 10.4 Hz) 3.49 |
| Rha | | |
| 1'''' | 101.85 | 4.53 (H1'''', brs) |
| 2'''' | 71.34 | 3.38 (H2'''', m) |
| 3'''' | 83.09 | 3.63 (H3'''', dd, J = 8.9, 2.2 Hz) |
| 4'''' | 72.6 | 3.46 (H4'''', m) |
| 5'''' | 69.49 | 3.54 (H5'''', m) |
| 6'''' | 18.08 | 1.12 (H6'''', d, J = 6.1 Hz) |

Figure 6:
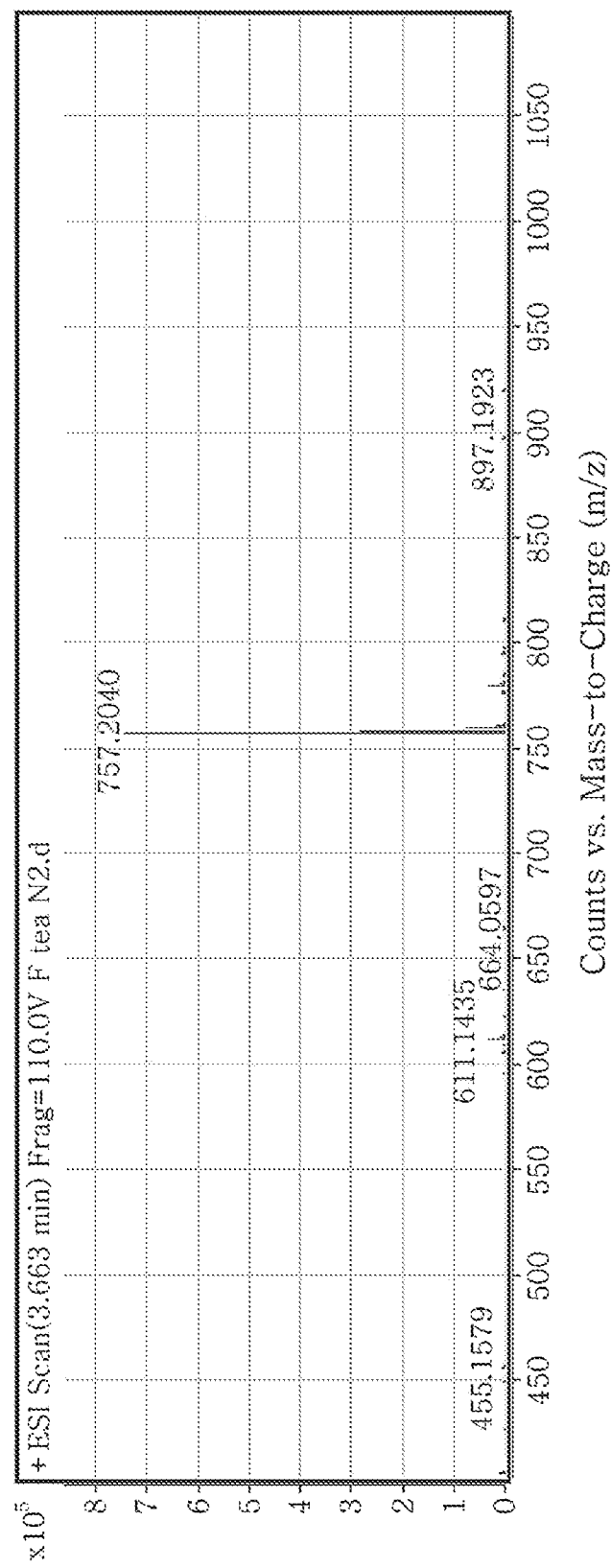
FIG. 6 shows the MS spectrum of quercetin 3-O-[3-O"-(E)-p-coumaroyl][α-L-rhamnopyranosyl-(1→6)-O-β-D-glucopyranoside].
Figure 7:
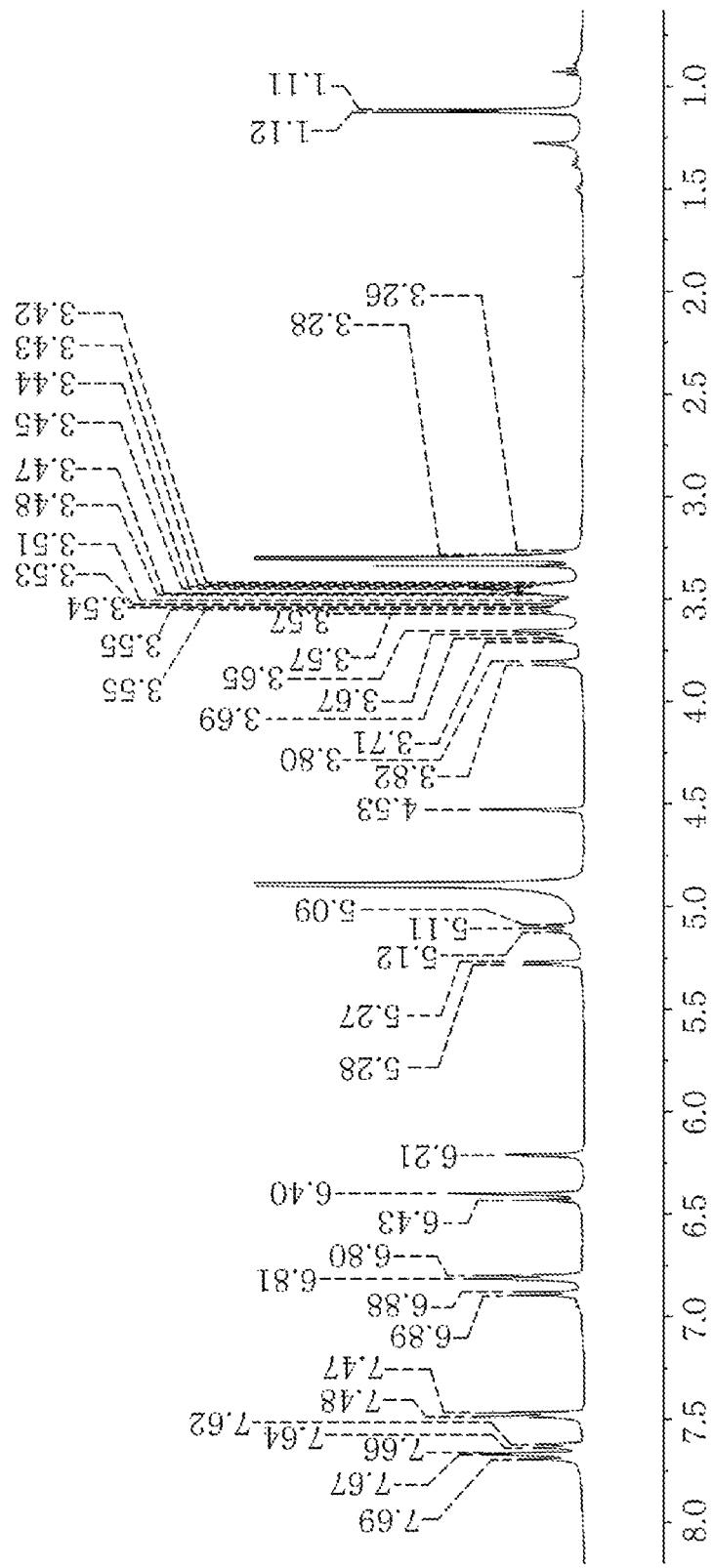
FIG. 7 shows the $^1$H-NMR spectrum of quercetin 3-O-[3-O"-(E)-p-coumaroyl][α-L-rhamnopyranosyl-(1→6)-O-@-D-glucopyranoside].
Figure 8:
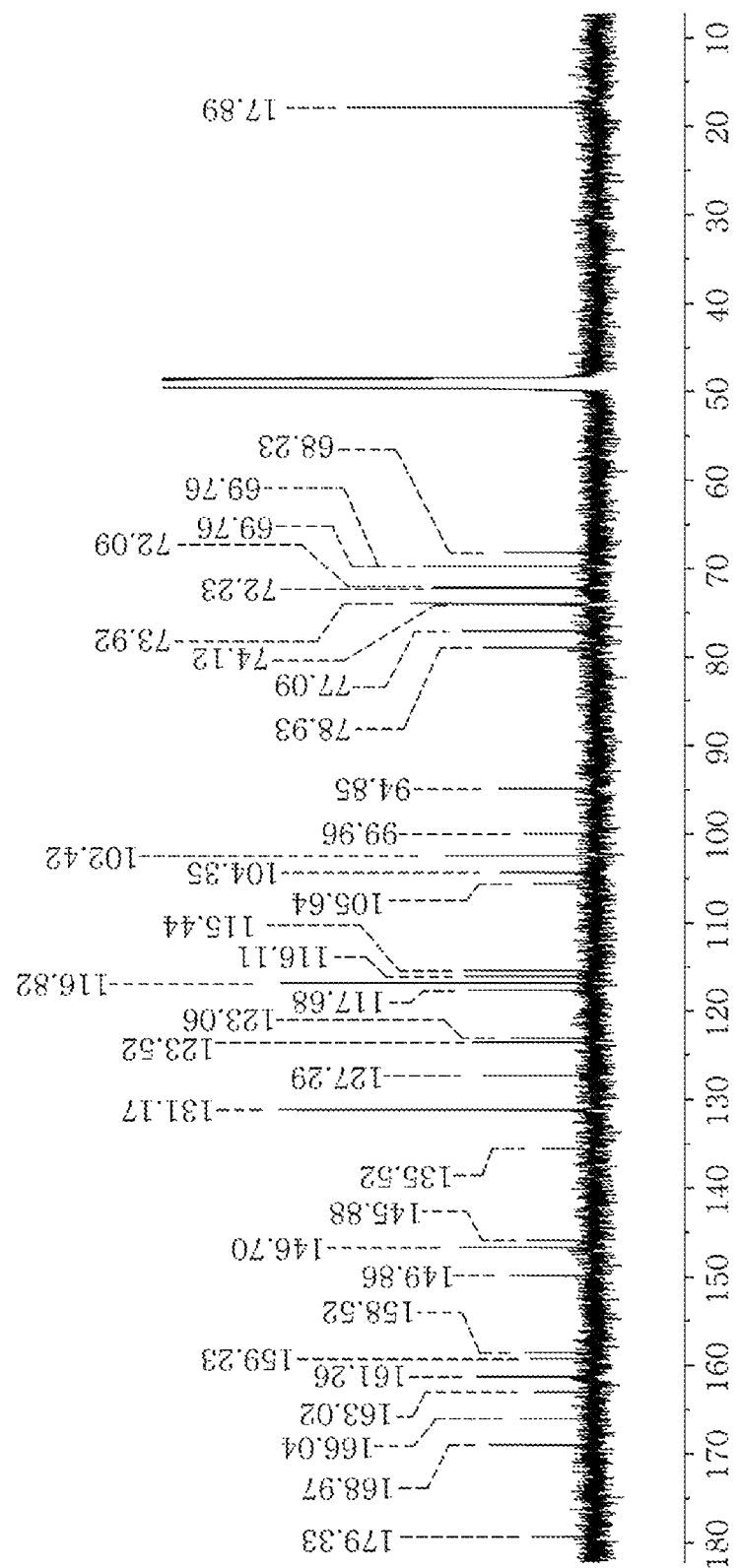
FIG. 8 shows the $^{13}$C-NMR spectrum of quercetin 3-O-[3-O"-(E)-p-coumaroyl][α-L-rhamnopyranosyl-(1→6)-O-β-D-glucopyranoside].
Figure 9:
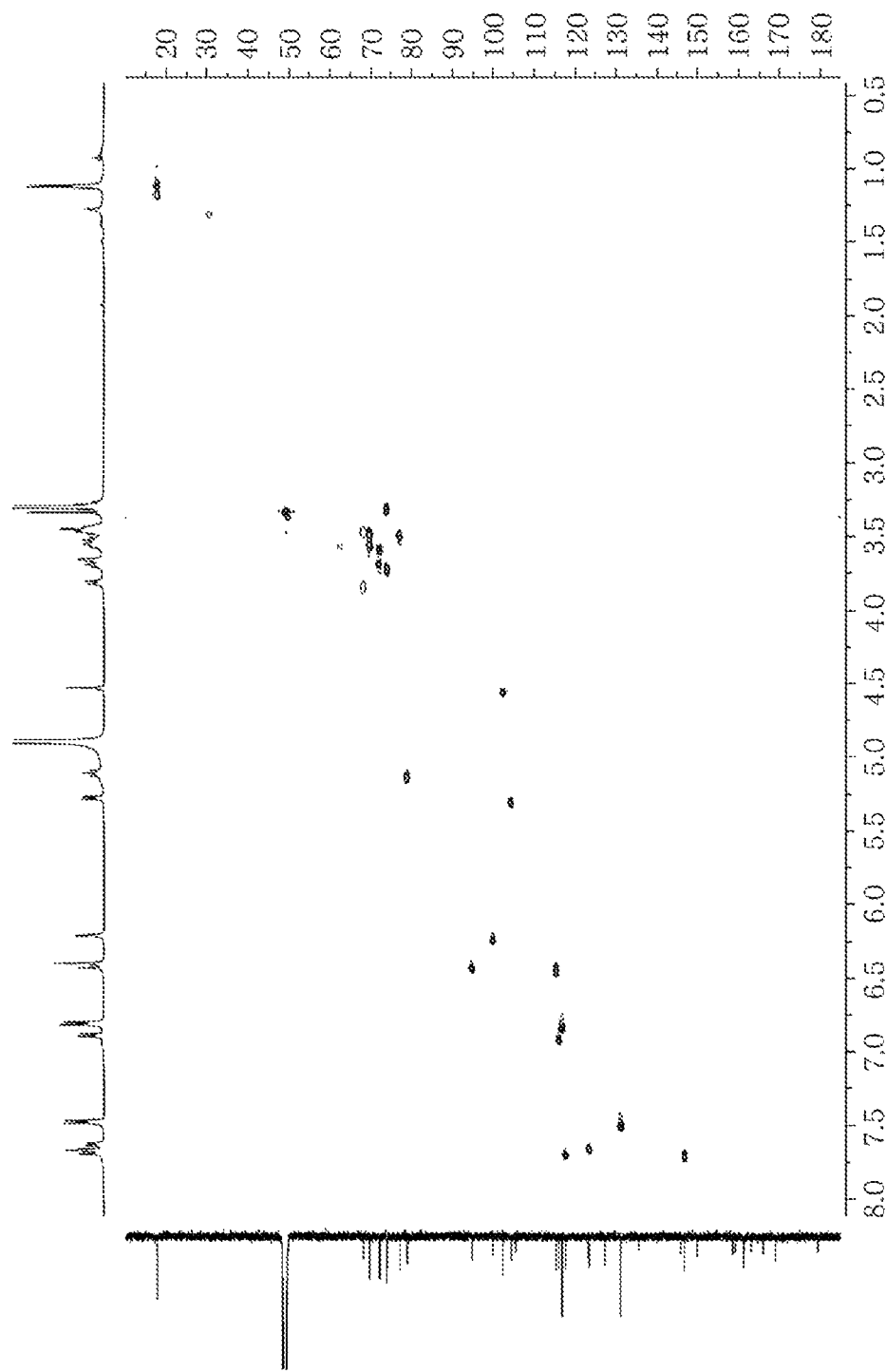
FIG. 9 shows the $^1$H-$^{13}$C HSQC (heteronuclear single quantum coherence) spectrum of quercetin 3-O-[3-O"-(E)-p-coumaroyl][α-L-rhamnopyranosyl-(1→6)-O-β-D-glucopyranoside].
Figure 10:
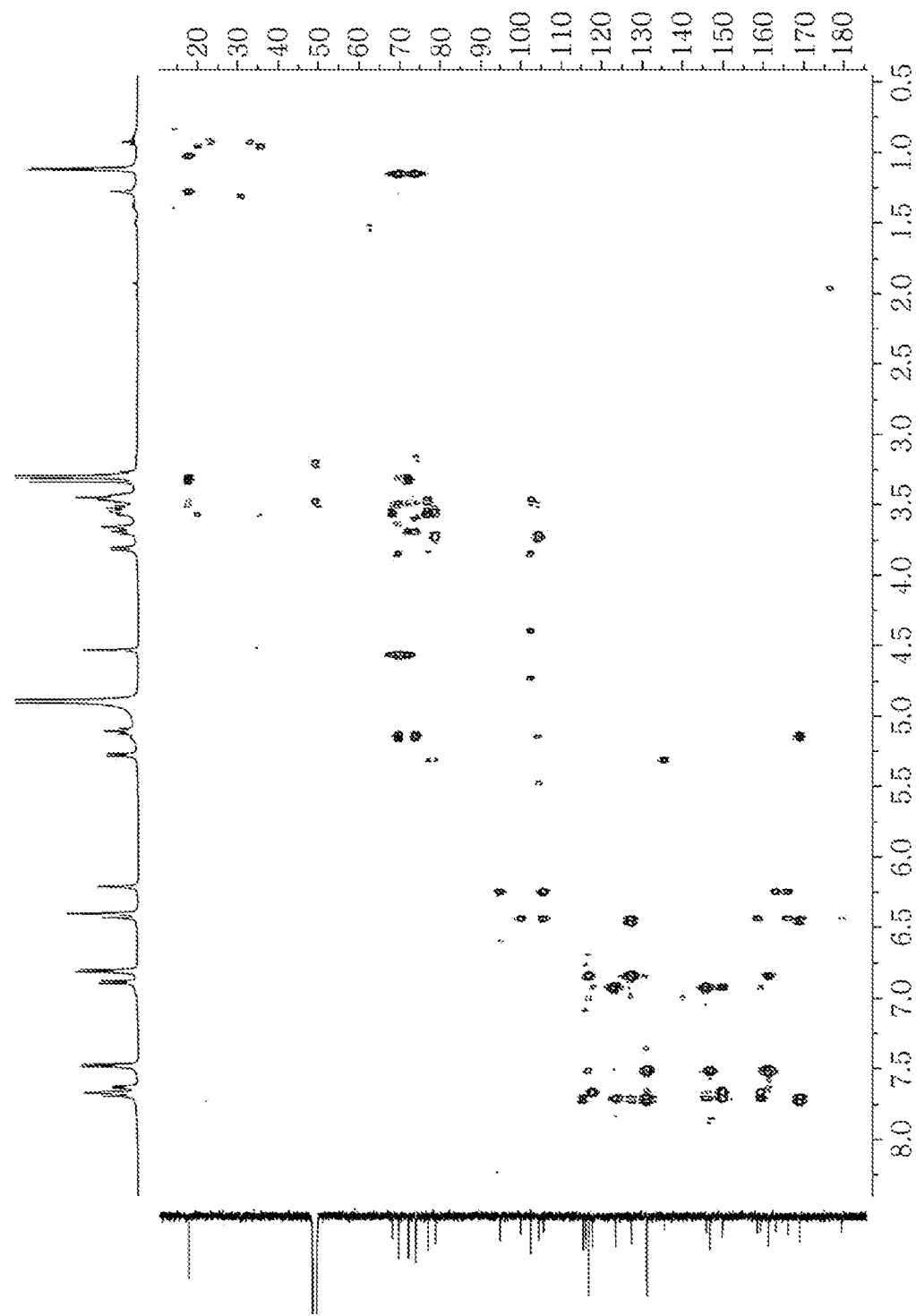
FIG. 10 shows the $^1$H-$^{13}$C HMBC (heteronuclear multiple-bond coherence) spectrum of quercetin 3-O-[3-O"-(E)-p-coumaroyl][α-L-rhamnopyranosyl-(1→6)-O-β-D-glucopyranoside].

The MS spectrum of quercetin 3-O-[3-O''-(E)-p-coumaroyl][α-L-rhamnopyranosyl-(1→6)-O-β-D-glucopyranoside] is as shown in FIG. 6, and the $^{1}$H-NMR spectrum and the $^{13}$C-NMR spectrum thereof are as shown in FIG. 7 and FIG. 8, respectively. The HSQC (heteronuclear single quantum coherence) spectrum thereof is as shown in FIG. 9, and the HMBC (heteronuclear multiple-bond coherence) spectrum thereof is as shown in FIG. 10.

Test Example 1: Confirmation of Beta-Amyloid Aggregation Inhibitory Effect

The beta-amyloid aggregation inhibitory effect of quercetin 3-O-[3-O''-(E)-p-coumaroyl][β-D-glucopyranosyl- (1→3)-O-α-L-rhamnopyranosyl-(1→6)-O-β-D-glucopyranoside] and quercetin 3-O-[3-O"-(E)-p-coumaroyl][α-L-rhamnopyranosyl-(1→6)-O-β-D-glucopyranoside] was determined by fluorescence analysis (Thioflavin T assay).

Specifically, β-amyloid (Aβ1-42, AnaSpec Inc, USA) was obtained and used at a concentration of 0.1 mg/ml. It was stored at −80° C. prior to use. Each of morin (20 μM), phenol red (20 μM), quercetin 3-O-[3-O"-(E)-p-coumaroyl][β-D-glucopyranosyl-(1→3)-O-α-L-rhamnopyranosyl-(1→6)-O-β-D-glucopyranoside] (1 mg/ml), and quercetin 3-O-[3-O"-(E)-p-coumaroyl][α-L-rhamnopyranosyl-(1→6)-O-β-D-glucopyranoside] (1 mg/ml) was diluted to these concentrations in DMSO. In order to determine the degree of inhibition of Aβ1-42 aggregation, each compound at the above concentration was diluted to 10 μM in 50 μL of 0.01 M sodium phosphate buffer solution. Then, 40 μL of 0.1 mg/ml Aβ1-42 was added thereto, followed by addition of 10 μL of 2 mM Thioflavin T. The fluorescence was then measured with a fluorescence spectrometer (RF-5300PC, SHIMADZU CORPORATION, Japan) at 37° C. and intervals of 5 minutes for 150 minutes.

Figure 11:
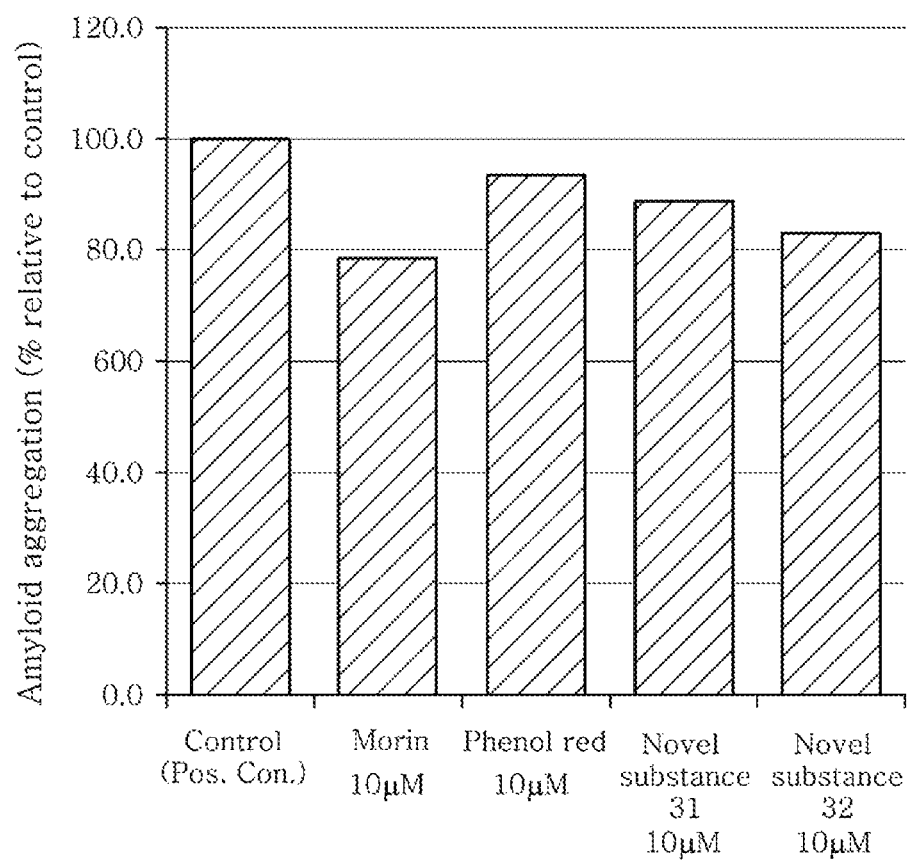
FIG. 11 shows the effect of the compound according to one aspect of the present invention on the aggregation of beta amyloid.

The results are shown in the table below and FIG. 11.

TABLE 3

|  | Increased RFU | Increased RFU (% of Pos.Cont.) |
|---|---|---|
| Pos.Cont. | 14595 | 100.0 |
| Novel substance 31 | 12955 | 88.8 |
| Novel substance 32 | 12148 | 83.2 |
| Morin | 11471 | 78.6 |
| Phenol Red | 13655 | 93.6 |

In the table above, "RFU" denotes relative fluorescence unit, and "increased RFU" indicates the amount of aggregated β-amyloid. "Increased RFU (% of Pos.Cont.)" indicates the percentage of aggregated β-amyloid compared to the positive control. "Novel substance 31" indicates quercetin 3-O-[3-O"-(E)-p-coumaroyl][β-D-glucopyranosyl-(1→3)-O-α-L-rhamnopyranosyl-(1→6)-O-β-D-glucopyranoside], and "novel substance 32" indicates quercetin 3-O-[3-O"-(E)-p-coumaroyl][α-L-rhamnopyranosyl-(1→6)-O-β-D-glucopyranoside].

When the aggregation of the positive control (indicated by "Pos.Cont.", aggregation of beta amyloid without treatment with the compounds) was taken as 100%, quercetin 3-O-[3-O"-(E)-p-coumaroyl][β-D-glucopyranosyl-(1→3)-O-α-L-rhamnopyranosyl-(1→6)-O-β-D-glucopyranoside] and quercetin 3-O-[3-O"-(E)-p-coumaroyl][α-L-rhamnopyranosyl-(1→6)-O-β-D-glucopyranoside]decreased aggregation by 11.2% and 16.8%, respectively, compared with the positive control. This result indicates that the substances are as excellent as the known inhibitors, morin (21.4%) and phenol red (6.4%) in inhibiting beta-amyloid aggregation. Thus, the two compounds have the above usefulness and thus can be used in various industrial fields.

Test Example 2: Cumulative Skin Irritation Test

HRIPT (human repeated insult patch test) was performed to evaluate the cumulative skin irritation of quercetin 3-O-[3-O"-(E)-p-coumaroyl][β-D-glucopyranosyl-(1→3)-O-α-L-rhamnopyranosyl-(1→6)-O-β-D-glucopyranoside] and quercetin 3-O-[3-O"-(E)-p-coumaroyl][α-L-rhamnopyranosyl-(1→6)-O-β-D-glucopyranoside] and determine the range of concentration applicable to the skin.

Specifically, 15 healthy adult subjects were randomly selected, and 20 μl of a test composition (composition for the skin including an emulsifier, a stabilizer, purified water, etc. in addition to each of the above compounds) containing 0.5% by weight, 1% by weight or 3% by weight of each of the compounds was dropped into each chamber (IQ chamber, Epitest Ltd, Finland) The patch was applied to the upper right side of the back of the subject, and after 24 hours from the application, it was replaced with a new patch. In this way, a total of 9 patches were applied, 3 times a week for 3 weeks. The skin reaction was checked before and after application of each patch. The skin reaction was checked until after 48 hours from the removal of the final patch, and the average reactivity was calculated.

The results are shown in the table below.

TABLE 4

| Test substance and its content | Number of subjects showing ±, + or ++ reactivity (unit: number of persons) | | | | | | | | | Average reactivity |
|---|---|---|---|---|---|---|---|---|---|---|
| | 1st | 2nd | 3rd | 4th | 5th | 6th | 7th | 8th | 9th | |
| Control | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |
| 0.5% by weight of novel substance 31 | 0 | 0 | 0 | 0 | 0 | 0 | 0 | 0 | 0 | 0 |
| | 0 | 0 | 0 | 0 | 0 | 0 | 0 | 0 | 0 | |
| 1% by weight of novel substance 31 | 0 | 0 | 0 | 0 | 0 | 0 | 0 | 0 | 0 | 0 |
| | 0 | 0 | 0 | 0 | 0 | 0 | 0 | 0 | 0 | |
| 3% by weight of novel substance 31 | 0 | 0 | 0 | 0 | 0 | 0 | 0 | 0 | 0 | 0 |
| | 0 | 0 | 0 | 0 | 0 | 0 | 0 | 0 | 0 | |
| 0.5% by weight of novel substance 32 | 0 | 0 | 0 | 0 | 0 | 0 | 0 | 0 | 0 | 0 |
| | 0 | 0 | 0 | 0 | 0 | 0 | 0 | 0 | 0 | |
| 1% by weight of novel substance 32 | 0 | 0 | 0 | 0 | 0 | 0 | 0 | 0 | 0 | 0 |
| | 0 | 0 | 0 | 0 | 0 | 0 | 0 | 0 | 0 | |
| 3% by weight of novel substance 32 | 0 | 0 | 0 | 0 | 0 | 0 | 0 | 0 | 0 | 0 |
| | 0 | 0 | 0 | 0 | 0 | 0 | 0 | 0 | 0 | |

Reactivity
−: Negative (no reaction)
±: Suspicious or slight erythema, etc.
+: Weak reaction (not accompanied by vesicles), erythema, papules
++: Severe reaction (accompanied by vesicles), erythema, papules, vesicles
+++: Strong reaction, bullae
Average reactivity equation
Average reactivity = [{(Sum of the values obtained by multiplying the number of subjects who showed reactivity by the reaction quotient)/(Number of total subjects × Highest score (4 points))} × 100]/Number of examinations (9 times)
If the reactivity is −, the reaction quotient is 0; if the reactivity is ±, the reaction quotient is 1; if the reactivity is +, the reaction quotient is 2; and if the reactivity is ++, the reaction quotient is 4.
If the average reactivity is less than 3, the composition is determined to be safe.

The skin reaction was evaluated according to the criteria of the International Contact Dermatitis Research Group (ICDRG). In the above table, "novel substance 31" denotes quercetin 3-O-[3-O"-(E)-p-coumaroyl][β-D-glucopyranosyl-(1→3)-O-α-L-rhamnopyranosyl-(1→6)-O-β-D-glucopyranoside], and "novel substance 32" denotes quercetin 3-O-[3-O"-(E)-p-coumaroyl][α-L-rhamnopyranosyl-(1→6)-O-β-D-glucopyranoside. Within the content range, both of the substances showed (−) reactivity (no subject showed ±, +, ++, or +++ reactivity), which indicates that the substances do not cause cumulative skin irritation and thus can be safely used on the skin.

While the present invention has been described with respect to the specific embodiments, it will be apparent to those skilled in the art that the above descriptions are only preferred embodiments and that the scope of the present invention is not limited thereto.

The invention claimed is:

1. A compound represented by the following formula 1, a pharmaceutically acceptable salt thereof, a hydrate thereof or a solvate thereof:

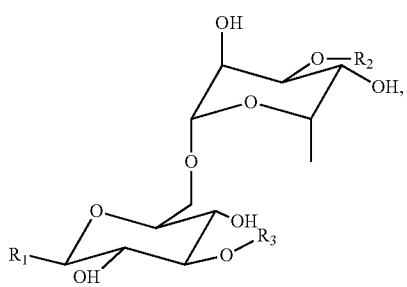

Formula 1 wherein $R_1$ is a compound represented by the following formula 2:

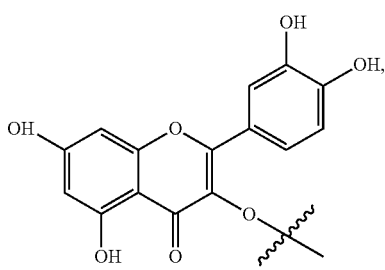

Formula 2

$R_2$ is H or a compound represented by the following formula 3:

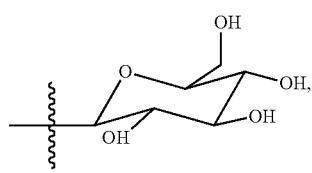

Formula 3 and $R_3$ is a compound represented by the following formula 4:

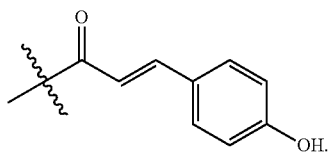

Formula 4

2. The compound, a pharmaceutically acceptable salt thereof, a hydrate thereof or a solvate thereof according to claim 1,
wherein the compound is quercetin 3-O-[3-O"-(E)-p-coumaroyl][β-D-glucopyranosyl-(1→3)-O-α-L-rhamnopyranosyl-(1→6)-O-β-D-glucopyranoside.

3. The compound, a pharmaceutically acceptable salt thereof, a hydrate thereof or a solvate thereof according to claim 1,
wherein the compound is quercetin 3-O-[3-O"-(E)-p-coumaroyl][α-L-rhamnopyranosyl-(1→6)-O-β-D-glucopyranoside].

4. A method for preparing a compound represented by the following formula 1, a pharmaceutically acceptable salt thereof, a hydrate thereof or a solvate thereof according to claim 1, comprising fermenting green tea and then separating it:

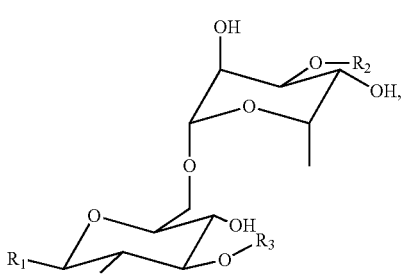

Formula 1 wherein $R_1$ is a compound represented by the following formula 2:

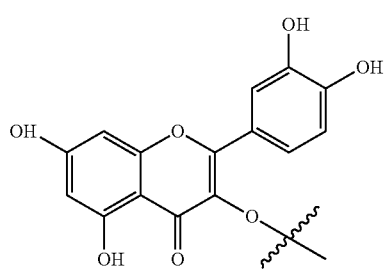

Formula 2

$R_2$ is H or, a compound represented by the following formula 3:

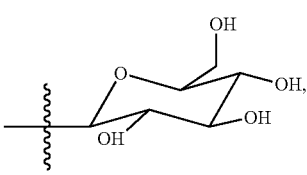

Formula 3 and $R_3$ is a compound represented by the following formula 4:

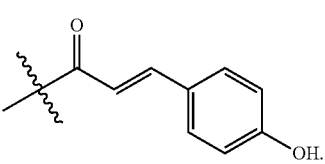

Formula 4

5. The preparation method according to claim 4, wherein the fermentation is performed by a post-fermentation method.

6. The preparation method according to claim 4, wherein the compound is quercetin 3-O-[3-O"-(E)-p-coumaroyl][β-D-glucopyranosyl-(1→3)-O-α-L-rhamnopyranosyl-(1→6)-O-β-D-glucopyranoside.

7. The preparation method according to claim 4, wherein the compound is quercetin 3-O-[3-O"-(E)-p-coumaroyl][α-L-rhamnopyranosyl-(1→6)-O-β-D-glucopyranoside].

* * * * *